United States Patent [19]
Silagy et al.

[11] Patent Number: 5,226,918
[45] Date of Patent: Jul. 13, 1993

[54] PROSTHESIS WITH ADJUSTABLE FITTING CLEARANCE

[76] Inventors: Howard Silagy, 265 Post Ave., Westbury, N.Y. 11590; John F. Lenze, 444 Community Dr., Manhasset, N.Y. 11030

[21] Appl. No.: 912,728

[22] Filed: Jul. 13, 1992

[51] Int. Cl.⁵ .......................... A61F 2/60; A61F 2/78
[52] U.S. Cl. ...................................... 623/32; 623/27; 623/33; 623/38; 623/57
[58] Field of Search ................................. 623/33-35, 623/38, 32, 27, 57

[56] References Cited
U.S. PATENT DOCUMENTS

| | | | |
|---|---|---|---|
| 980,457 | 1/1911 | Toles | 623/34 X |
| 1,211,423 | 1/1917 | Eisen | 623/33 |
| 1,477,484 | 12/1923 | Harrison | 623/32 |
| 2,669,728 | 2/1954 | Ritchie | 623/33 X |
| 3,400,408 | 9/1968 | Garcia | 623/38 X |
| 3,947,897 | 4/1976 | Owens | 623/27 X |

Primary Examiner—Ronald Frinks

[57] ABSTRACT

A prosthesis for attachment with an adjustable fitting clearance to an amputation stump in which optionally, the fit therebetween can be diminished by connectors threadably engaged with each other one thread at a time, or the fit totally released by correspondingly releasing the threaded engagment of the connectors.

3 Claims, 3 Drawing Sheets

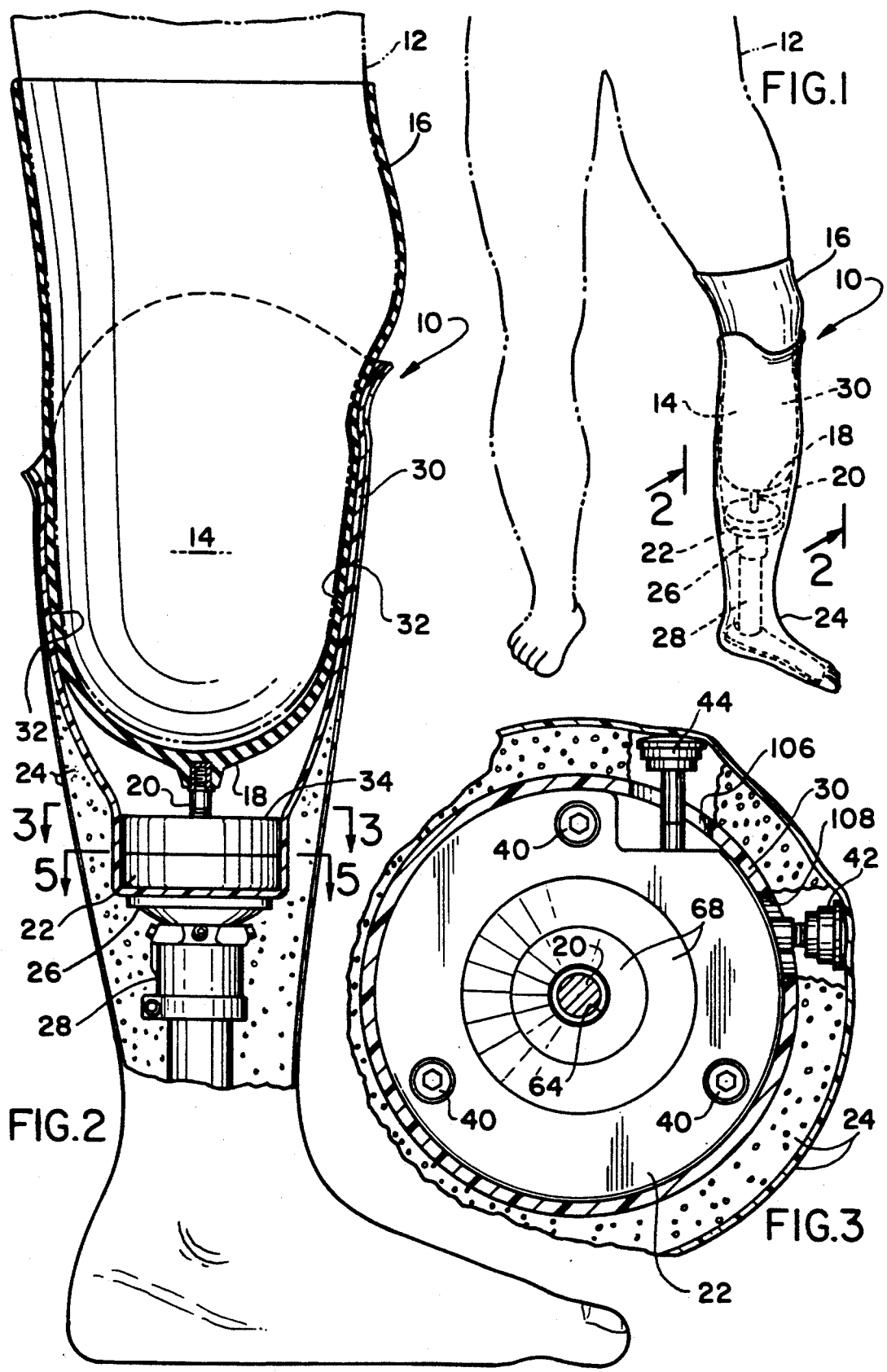

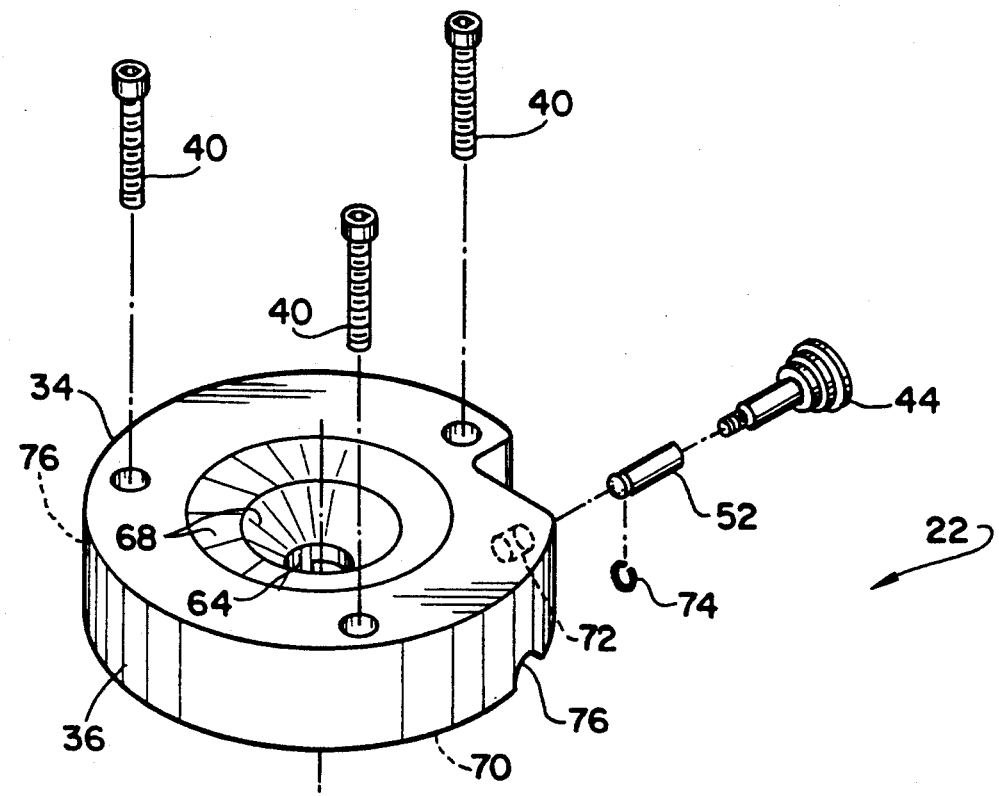
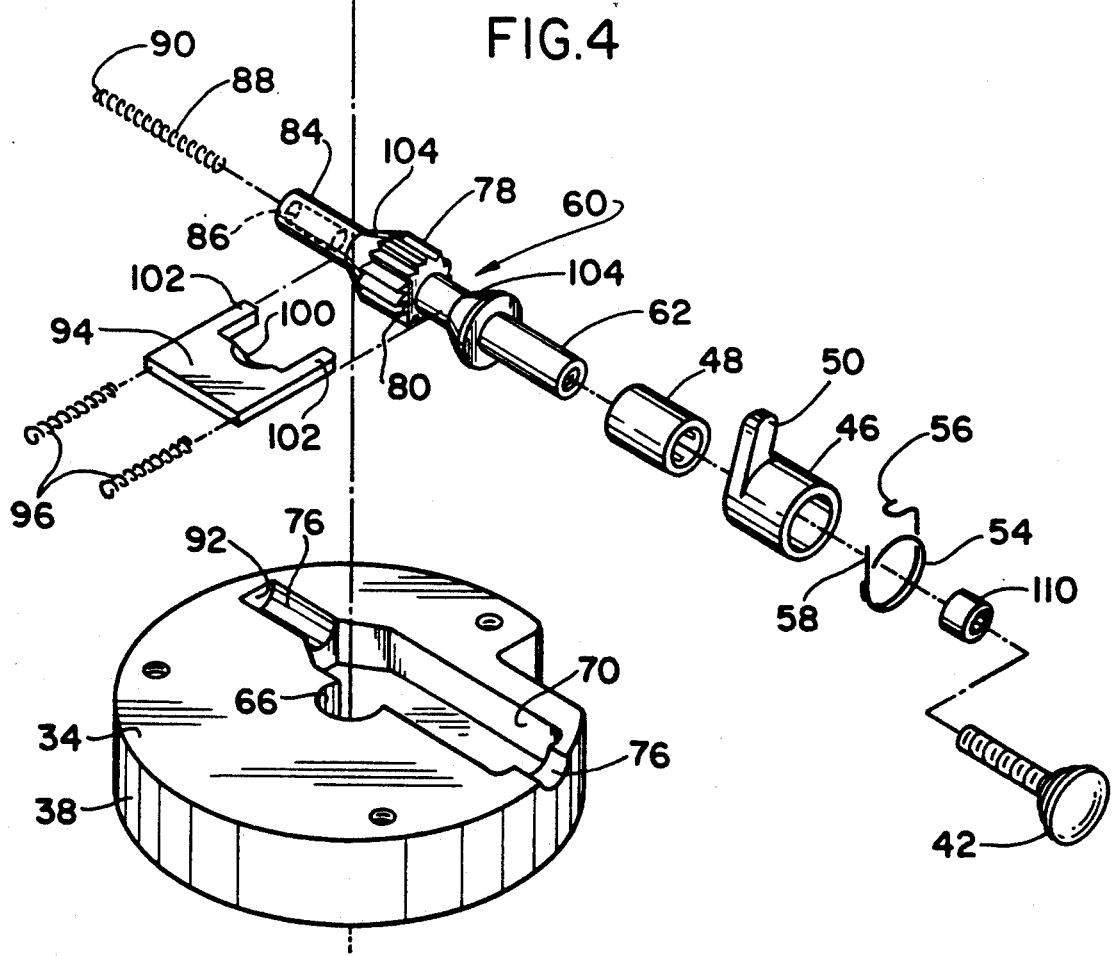
FIG.4

PROSTHESIS WITH ADJUSTABLE FITTING CLEARANCE

The present invention relates to improvements in an artificial arm or leg prosthesis in which, more particularly, the improvements facilitate adjustments in the fitting clearance, i.e. whether "tight" or "loose", in which the amputation stump is received in the prosthesis.

EXAMPLE OF THE PRIOR ART

A prosthesis generally similar to the prosthesis hereof is illustrated and described in U.S. Pat. No. 3,947,897 issued on Apr. 6, 1976 to Owens.

The Owens prosthesis uses a lock pin 30 inserted in a female socket 16 seated in an amputation stump bone 12. The lock pin 30 has at its upper end retractable balls 28 for completing its attachment to socket 16.

The only "adjustment" in relative position between the amputation stump and the prosthesis is limited to the clearance of the openings receiving the balls 28, as described in column 3, lines 51-58.

Broadly, it is an object of the present invention to overcome the foregoing and other shortcomings of the prior art by providing a prosthesis that is adjustable through an extensive range of fitting clearances between the amputation stump and the cooperating prosthesis.

More particularly, it is an object to provide for facilitated quick release of the prosthesis from the amputation stump incident to loosening the fit therebetween, and to establish a standardized discrete extent of closing movement therebetween incident to tightening the fit therebetween, i.e. achieving the closing movement in multiples of these standardized discrete movements, so that over all the fit can be tightened according to the comfort requirements of the user.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is an overall perspective view showing the within inventive improved prosthesis device in use on a leg amputation stump;

FIG. 2 is an enlarged scale cross sectional view as taken along line 2—2 of FIG. 1;

FIG. 3 is an even still larger enlarged scale cross sectional view as taken along line 3—3 of FIG. 2;

FIG. 4 is an exploded perspective view of the components in isolated perspective of the coupling device of the prosthesis;

Figure 5:
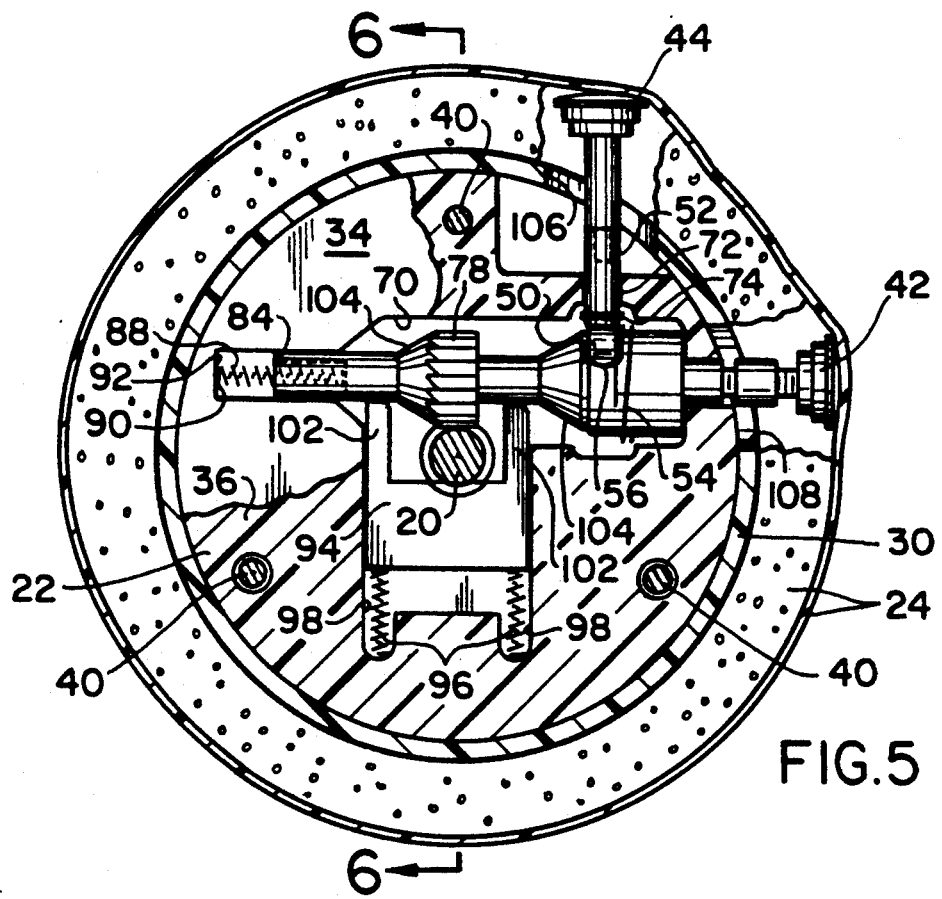
FIG. 5 is a cross sectional view on the same scale as FIG. 3 as taken along line 5—5 of FIG. 2.

As shown in FIGS. 1 and 2, the invention is demonstrated as a lower leg prosthesis worn by a user 12 partly outlined in phantom prospective, it being understood that a prosthesis embodying the improvements of the present invention could also be used or worn on an amputation stump of an arm. In the specific application illustrated, a left leg amputation stump 14 is contained in an elastic soft rubber bladder or sock 16. Sock 16 is snug fitting and has an airtight fit about stump 14 and, as is well understood, has a conforming shape to contribute to providing a comfortable fit for the user. Typically, this is enhanced by using a soothing, sealant-like, antibacterial cream which is previously applied to stump 14 before sleeve 16 is placed thereon. The lower end 18 of sock 16 is provided in any appropriate manner with a first connector or cylindrically shaped locking pin 20 having annular grooves 82 and also an operative position in which it extends in depending relation from sock 16 through aligned through bores 64,66 forming a cylindrical opening of a second connector 34,36 in which it can advantageously be used to engage external teeth 80 of a rotatable member or shaft 60 functioning as a coupling mechanism, generally designated 22, and to be described in detail as this description proceeds.

At this point it is helpful to note that prosthesis 10 is embodied with the shape, size and appearance of a natural lower leg. Accordingly, and as is well understood, surface materials 24 are of laminated plastic and foam which are supported on an internal structural frame 26. The lower portion or section 28 of this support frame is made of lightweight metal members simulating a natural ankle and foot. The upper structural part of prosthesis 10 consists of a rigid plastic cup 30 thermal formed to the shape of the amputation stump 14. As best seen in FIG. 2, an internal surface 32 of the amputation stump-receiving cup 30 is tapered to enhance its weight-bearing capacity function. Additionally, the lower end of cup 30 is also thermal formed about the coupling mechanism 22 and, thus, effectively serves as a housing for the coupling mechanism 22. Typically, before surface finishing materials 24 are applied to the prosthesis 10, structural members 26 are adjusted vertically and axially to provide the most natural stance, and accommodate other such considerations, of the user 12.

For well understood reasons it is known that in the use of a prosthesis, such as prosthesis 10 hereof, there will be occasions, particularly during resting periods, when the amputation stump 14 tends to enlarge and consequently will become uncomfortably tight within cup 30. On the other hand, during an arduous weight-bearing period, stump 14 has been known to contract and, consequently, provide a "loose" fit within cup 30, which is also perceived by the user as a fit which is uncomfortable and, therefore, undesirable. It is accordingly a significant objective of the present invention to provided the coupling mechanism 22 which, as will be subsequently described in detail, allows the user to conveniently and inconspicuously adjust the prosthesis 10 to obviate the "tight" and "loose" fits above noted. That is, locking pin 20 can easily be released from coupling 22 to allow the stump 14 to be "backed out" of cup 30, it being recommended that this be done while the user is sitting, and an adjustment can just as easily be made in which the locking pin 20 can be advanced within the coupling mechanism 22, thus drawing the stump 14 into a further projected position within cup 30 and thus against the interior tapered surface 32 of the cup, a position adjustment that it is recommended that the user make in anticipation of, or even during use of, the prosthesis in an arduous weight-bearing mode.

Description will now be made of the specific components of coupling mechanism 22 providing the two opposite direction adjustments of the fitting clearance between the amputation stump 14 and prosthesis 10 just noted, this description being best understood with specific reference to FIG. 4. More particularly, coupling mechanism 22 includes what can be aptly termed a housing 34 which, in turn, is comprised of an upper disc-shaped member 36 which is assembled to a lower base plate 38 by three machine screws 40. In relation to releasing the "tight fit" previously referred to, another provided component is a release button 42 shown in FIG. 4 in its operative position in relation to the assembled coupling mechanism 22, but which will be understood is not part of the initial assembly of the mechanism 22, but rather is assembled subsequently. First, however, it is recommended that there be an initial or pre-assembly in which an actuator sleeve 46 is press fitted to a roller clutch 48 of any type that is commercially available, such as the clutch manufactured by The Torrington Company of Torrington, Conn. and identified by catalog number RC-040708.

Actuator sleeve 46 has a side extension arm 50 which fits within a clearance cavity 70 provided in the confronting surface of upper member 36 with lower plate 38 and which arm 50 interacts with actuator pin 52 when button 44 is pressed. After sleeve 46 is press fitted to clutch 48, one end of a torque spring 54 is encircled about sleeve 46 and the hooked end portion thereof is disposed in engaged relation to the extension arm 50. Next in the assembly process, the other or opposite end 58 of spring 54 is seated against the interior of upper member 36, thus biasing arm 50, sleeve 46 and clutch 48 in a clockwise direction, as seen in FIG. 4, the significance of which is that the arm 50 occupies an operable position in which it can be contacted by a pin extension 52 of button 44, thus resulting in a cranking or a reciprocating pivotal traverse which, as will be subsequently explained, results in providing one of the adjustments in the fitting clearance space, namely the urging in descending movement of the amputation stump 14 into the prosthesis 10. As a final step in the assembly, clutch 48, sleeve 46 and spring 54 are slipped over the end 62 of shaft 60.

It will be noted that both upper housing member 36 and lower base plate 38 have respective aligning centrally located throughbores 64 and 66, respectively, which through-bores are adapted to receive in projected relation the locking pin 20 of the cup 30. To facilitate the projecting of the locking pin 20, the upper surface of member 36 has a lead-in countersink 68. Both members 36 and 38 have, on confronting surfaces, a clearance cutout 70 to accommodate internally disposed components of the coupling mechanism 22.

Figure 6:
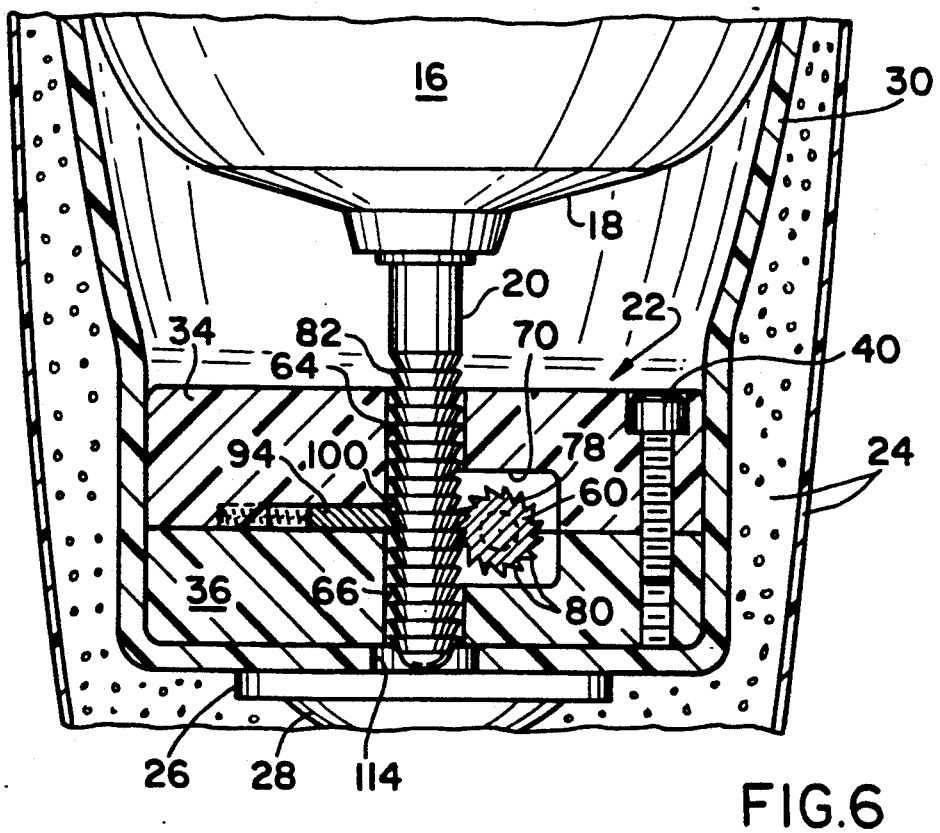
FIG. 6 is a partial cross sectional view as taken along line 6—6 of FIG. 5.

Still referring to FIG. 4, it is to be understood that shaft 60 is rotatably fitted within housing 34 on opposite end bearing saddles 76. The longitudinal axis of shaft 60 is located in an offset relation from the vertical axis of the through-bores 64 and 66, which has the effect of locating a ratchet section 78 in a cooperating meshing engagement with pin 20. Thus, as best seen in FIG. 6, ratchet section 78 has machined teeth providing spaced grooves 80 oriented parallel to the longitudinal axis of shaft 60 and thus adapted to engage corresponding teeth or annular grooves 82 appropriately provided, as by machining or otherwise on pin 20.

The end 84 of shaft 60 is provided with a blind bore 86 in which there is seated or retained a compression spring 88. At assembly, the free or unseated end 90 of spring 88 bears against surface 92 at the end of the one bearing saddle 76 and thus provides the urgency or bias to urge shaft 60 in the direction of movement to the right as viewed in FIGS. 4 and 5.

To retain pin 20 from disengaging from the coupling mechanism 22 in response to the just mentioned urgency, a locking plate 94 is located so as to automatically latch against a selected one tooth of the annular circumferential arrangement of teeth 82. Plate 94 is biased towards pin 20 and shaft 60 by a pair of compression springs 96 which are seated or retained within spaced apart recesses 98 provided in upper housing member 36. An inclined contoured edge 100 on plate 94 allows plate 94 to be urged in movement to the left, as viewed in FIG. 6, and then relatched as pin 20 is advanced in depending movement downward when actuated to do so.

It will, of course, be understood that, when roller clutch 48 is in gripping engagement with the shaft section 62, counterclockwise rotation (as viewed in FIGS. 4 and 6) of ratchet section 78 will correspondingly cause pin 20 to be drawn down into coupling mechanism 22, this in turn being a consequence of actuator button 44 being pressed and in turn causing pin 52 to bear against extension arm 50 on actuator sleeve 46. Stated otherwise, the contact of pin 52 against extension arm 50 produces a cranking or pivotal traverse in shaft 60 and thus in the ratchet section 78, and this causes pin 20 to advance one annular tooth or groove 82 at a time. After each such advance, pin 20 is again held against movement or in its last position of movement by the projection of edge 100 of locking plate 94 within the spacing between adjacent ratchet teeth 80.

Plate 94 is also provided with a pair of cam follower extension arms 102 which are strategically positioned to cooperate with conical cam surfaces 104 on shaft 60. More particularly, and as best seen in FIGS. 4 and 5, it will be understood that, when release button 42 is pressed, shaft 60 moves to the left compressing spring 88, and this movement releases ratchet section 78 from its engagement with teeth 82 on pin 20 while simultaneously urging locking plate 94 into a clearance position from pin 20 via cams 104 and follower arms 102. This results in the release of pin 20 from the coupling mechanism 22, and, thus, in a loosening of the fitting clearance between the amputation stump 14 and the prosthesis 10.

From the preceding description, it is to be understood that all components of the coupling mechanism 22 are in assembled relation, except for actuator button 44 and release button 42. It is to be noted at this point that assembly 22 is thermo formed within the base of cup 30. Upon cooling, clearance holes 106 and 108 are located and drilled through cup 30 (FIGS. 3 and 5). Holes 106 and 108 are used to achieve the installation of actuator button 44 and release button 42. A guide sleeve 110 is also installed with button 42. On the lower surface of cup 30, the necessary holes are made for attachment of flange 26 (FIG. 2) between base plate 38 and lower structural member 28. Additionally, a clearance hole 114 is made for pin 20. Accordingly, final adjustments are possible to be made to accommodate to the aesthetic requirements of the user which are significant in dictating the manner in which the surface materials 24 are laminated into place. In FIGS. 3 and 5 it is to be noted, for example, that the "skin" simulated by the materials 24 is slightly raised in the vicinity of buttons 44 and 42. This slight protrusion allows the user of the prosthesis 10 to easily "feel" and thus locate the actuator button 44 and also the release button 42. Thus, even though these buttons are not external of the prosthesis 10 and thus are masked from view which is an important requirement for aesthetic purposes, these buttons nevertheless are readily accessible (by feel) and can therefore be actuated to make the necessary adjustments in the fitting clearance between the amputation stump 14 and prosthesis 10, whether it be to obviate an undesirable "tight" or an undesirable "loose" fit.

For completeness sake, it is mentioned that, when prosthesis 10 is completed and the user 12 is accustomed to the device, a typical sequence of use might be in accordance with the following scenario. On arising, the stump 14 is inspected for any visible abrasions, rashes, or the like. A recommended cream or lotion is applied to stump 14 and rubber bladder 16 is drawn thereover. Next, stump 14 is guided within cup 30 so that pin 20 assumes its operative position in which it is projected into coupling mechanism 22. Actuator button 44 is then actuated externally by being pressed by feel through the outer "skin" of the prosthesis, the number of times in which this button is pressed being a function of the extent of advancement of the pin 20 through descending movement into the coupling mechanism 22 to provide a fit that feels comfortable in the manner in which the amputation stump fits into the cup 30.

During use, and particularly a period of weight-bearing use, the user 12 may feel that the prosthesis 10 has loosened. This will dictate the pressing of button 44 to draw pin 20 further within coupling mechanism 22, and thus to draw the now contracted amputation stump 14 further into cup 30.

After a protracted period of weight-bearing use, the user 12 may then feel it convenient or necessary to rest in a sitting or non-weight bearing mode. It is at this time that the amputation stump 14 may tend to swell or feel tight within cup 30 and the user 12 then has the option of pressing release button 42, again in an external manner, by feeling for it though the simulated "skin" of the prosthesis, and having located it in this manner, pressing the release button 42. As already described, pin 20 accordingly becomes disengaged from the coupling mechanism 22 and stump 14 is now able to be urged through ascending movement from cup 30 to whatever extent is required to increase the fitting clearance between the stump 14 and cup 30 to again restore a fit that feels comfortable to the user.

From the foregoing description, it should therefore be readily appreciated that adjustments, either tightening up or loosening up of the amputation stump with respect to the stump-receiving cup of the prosthesis 10 is an important operating mode of the prosthesis.

While the prosthesis 10 as described constructionwise and having the capacity for adjusting the fitting clearance with respect to an amputation stump, both of which have been herein shown and disclosed in detail, is fully capable of attaining the objects and providing the advantages hereinbefore stated, it is to be understood that it is merely illustrative of the presently preferred embodiment of the invention and that no limitations are intended to the detail of the construction or design herein shown other than as defined in the appended claims.

What is claimed is:

1. A prosthesis for attachment with an adjustable fitting clearance to an amputation stump comprising a first connector including a cylindrical member with annular grooves having an operative position adapted to extend in depending relation from an amputation stump for completing the attachment thereof to said prosthesis, a cooperating second connector having a cylindrical opening therethrough in a selected position on said prosthesis to receive in projected relation through said second connector opening said externally grooved member of said first connector, a transversely mounted rotatable member with external teeth disposed in meshing engagement with said externally grooved member of said first connector, first adjustment means for rotating said rotatable member in a direction of rotation for advancing said first connector grooved member at said meshing engagement contact therewith one groove at a time for correspondingly diminishing the fitting clearance between said amputation stump and said prosthesis the extent of each said groove advancement, and second adjustment means for slidably releasing said meshing interengagement between said rotatable member and said first connector grooved member incident to allowing enlargement of the fitting clearance between said amputation stump and said prosthesis, whereby selective operation of said first and second adjustment means enables the adjustment of the fitting clearance between said amputation stump and said prosthesis.

2. A prosthesis as claimed in claim 1 including a resilient skinlike surface thereon and said first and second adjustment means having internal operative positions thereagainst, to thereby permit the operation of said adjustment means by pressure contact thereagainst applied externally of the prosthesis resilient surface.

3. A prosthesis as claimed in claim 2 including a centrally located edge and legs on opposite sides thereof bounding a U-shaped configuration on a lock means normally spring biased to project said edge into locking relation with a selected groove of said first connector to hold said first connector in a position of movement, and cam means on said second adjustment means to cam an encountered leg of said lock means during sliding movement of said second adjustment means incident to slidably releasing said meshing engagement between said rotatable member and said first connector to correspondingly cause the unlocking of said first connector, whereby said first connector is released to allow enlargement of the fitting clearance between said amputation stump and said prosthesis.

* * * * *